(12) United States Patent
Wiser, III et al.

(10) Patent No.: US 12,214,364 B2
(45) Date of Patent: *Feb. 4, 2025

(54) FILTER MEDIA FOR ACTIVE FIELD POLARIZED MEDIA AIR CLEANER

(71) Applicant: Environmental Management Confederation, Inc., Princeton, NJ (US)

(72) Inventors: Forwood C. Wiser, III, Kingston, NJ (US); George R. Summers, Carleton Place (CA); Benjamin H. Kaeppner, Carleton Place (CA)

(73) Assignee: Environmental Management Confederation, Inc., Princeton, NJ (US)

( * ) Notice: Subject to any disclaimer, the term of this patent is extended or adjusted under 35 U.S.C. 154(b) by 126 days.

This patent is subject to a terminal disclaimer.

(21) Appl. No.: 17/322,979

(22) Filed: May 18, 2021

(65) Prior Publication Data

US 2021/0276021 A1 Sep. 9, 2021

Related U.S. Application Data

(63) Continuation of application No. 15/708,201, filed on Sep. 19, 2017, now Pat. No. 11,007,537, which is a
(Continued)

(51) Int. Cl.
*B03C 3/34* (2006.01)
*A61L 9/20* (2006.01)
(Continued)

(52) U.S. Cl.
CPC ............... *B03C 3/34* (2013.01); *A61L 9/205* (2013.01); *B03C 3/016* (2013.01); *B03C 3/09* (2013.01); *B03C 3/30* (2013.01); *B03C 3/64* (2013.01)

(58) Field of Classification Search
CPC .. B03C 3/34; B03C 3/016; B03C 3/09; B03C 3/30; B03C 3/64; A61L 9/205
See application file for complete search history.

(56) References Cited

U.S. PATENT DOCUMENTS 2,571,079 A 12/1948 Warburton
2,908,348 A 11/1957 Rivers et al.
(Continued)

FOREIGN PATENT DOCUMENTS

CA 1272453 8/1990
DE 339828 5/1985
(Continued)

OTHER PUBLICATIONS

Notice of Allowance issued in U.S. Appl. No. 15/708,201, mailed Jan. 22, 2021, 10 Pages.
(Continued)

*Primary Examiner* — Christopher P Jones
*Assistant Examiner* — Sonji Turner
(74) *Attorney, Agent, or Firm* — Schott, P.C.

(57) ABSTRACT

Filter media for an active field polarized media air cleaner includes two layers of dielectric material with a higher resistance air permeable screen sandwiched between the lower resistivity electric layers. The filter media may further include a mixed fiber filter layer having fibers from different sides of the triboelectric scale. The filter media may further include a layer of relatively higher density dielectric material followed by a layer of relatively lower density dielectric material.

14 Claims, 5 Drawing Sheets

Related U.S. Application Data continuation of application No. 14/451,531, filed on Aug. 5, 2014, now Pat. No. 9,764,331, which is a continuation of application No. 13/584,320, filed on Aug. 13, 2012, now Pat. No. 8,795,601, which is a continuation of application No. 12/732,626, filed on Mar. 26, 2010, now Pat. No. 8,252,095, which is a continuation of application No. 11/618,523, filed on Dec. 29, 2006, now Pat. No. 7,708,813.

(60) Provisional application No. 60/754,805, filed on Dec. 29, 2005.

(51) Int. Cl.
  *B03C 3/016* (2006.01)
  *B03C 3/09* (2006.01)
  *B03C 3/30* (2006.01)
  *B03C 3/64* (2006.01)

(56) References Cited

U.S. PATENT DOCUMENTS

| | | | | |
|---|---|---|---|---|
| 3,073,094 | A | 1/1963 | Landgraf et al. | |
| 3,471,695 | A | 10/1969 | Hudson et al. | |
| 3,509,696 | A | 5/1970 | Thompson | |
| 4,248,162 | A | 2/1981 | Skeist | |
| 4,322,232 | A | 3/1982 | Beane | |
| 4,357,150 | A | 11/1982 | Masuda et al. | |
| 4,549,887 | A | 10/1985 | Joannou | |
| 4,555,252 | A | 11/1985 | Eckstein | |
| 4,715,870 | A | 12/1987 | Masuda et al. | |
| 4,750,921 | A | 6/1988 | Sugita et al. | |
| 4,828,586 | A | 5/1989 | Joannou | |
| 4,853,005 | A | 8/1989 | Jaisinghani et al. | |
| 4,886,526 | A | 12/1989 | Joannou | |
| 4,886,527 | A | 12/1989 | Fottinger et al. | |
| 4,889,542 | A | 12/1989 | Hayes | |
| 4,902,306 | A | 2/1990 | Burnett et al. | |
| 4,978,372 | A * | 12/1990 | Pick | B03C 3/155 96/99 |
| 4,992,215 | A * | 2/1991 | Green | C08K 5/42 252/609 |
| 5,059,218 | A * | 10/1991 | Pick | E06B 9/52 160/381 |
| 5,108,470 | A * | 4/1992 | Pick | B03C 3/155 96/99 |
| 5,160,517 | A | 11/1992 | Hicks et al. | |
| 5,192,342 | A | 3/1993 | Baron et al. | |
| 5,223,006 | A | 6/1993 | Moran, III | |
| 5,240,478 | A | 8/1993 | Messina | |
| 5,322,473 | A | 6/1994 | Hofstra et al. | |
| 5,330,559 | A | 7/1994 | Cheney et al. | |
| 5,330,722 | A | 7/1994 | Pick et al. | |
| 5,336,299 | A | 8/1994 | Savell | |
| 5,360,469 | A | 11/1994 | Baron et al. | |
| 5,380,503 | A | 1/1995 | Fujii et al. | |
| 5,405,434 | A | 4/1995 | Inculet | |
| 5,417,433 | A | 5/1995 | Phillips | |
| 5,441,279 | A | 8/1995 | Messina | |
| 5,474,599 | A | 12/1995 | Cheney et al. | |
| 5,549,735 | A | 8/1996 | Coppom | |
| 5,562,286 | A | 10/1996 | Brinket | |
| 5,573,577 | A | 11/1996 | Joannou | |
| 5,593,476 | A * | 1/1997 | Coppom | B03C 3/155 96/88 |
| 5,616,172 | A | 4/1997 | Tuckerman et al. | |
| 5,627,376 | A | 5/1997 | Jaisinghani et al. | |
| 5,730,770 | A | 3/1998 | Greisz | |
| 5,807,425 | A * | 9/1998 | Gibbs | B03C 3/155 96/99 |
| 5,846,302 | A | 12/1998 | Putro | |
| 5,855,653 | A | 1/1999 | Yamamoto | |
| 5,858,045 | A | 1/1999 | Stemmer et al. | |
| 5,888,274 | A | 3/1999 | Frederick | |
| 5,942,017 | A | 8/1999 | Van Winkle, Sr. | |
| 5,997,619 | A | 12/1999 | Knuth et al. | |
| 6,056,809 | A * | 5/2000 | Chapman | B01D 46/0032 264/DIG. 48 |
| 6,063,167 | A | 5/2000 | Rutkowski | |
| 6,077,334 | A * | 6/2000 | Joannou | B03C 3/155 96/97 |
| 6,099,607 | A | 8/2000 | Haslebacher | |
| 6,245,126 | B1 * | 6/2001 | Feldman | B03C 3/155 95/278 |
| 6,294,004 | B1 * | 9/2001 | Summers | B01D 46/0032 55/DIG. 12 |
| 6,322,615 | B1 | 11/2001 | Chapman | |
| 6,328,788 | B1 | 12/2001 | Auger | |
| 6,428,610 | B1 | 8/2002 | Tsai et al. | |
| 6,464,760 | B1 | 10/2002 | Sham et al. | |
| 6,491,743 | B1 * | 12/2002 | Joannou | B03C 3/155 96/67 |
| 6,497,754 | B2 | 12/2002 | Joannou | |
| 6,514,324 | B1 * | 2/2003 | Chapman | B03C 3/28 55/528 |
| 6,544,309 | B1 | 4/2003 | Hoefer et al. | |
| 6,547,860 | B2 * | 4/2003 | Buchwald | D04H 1/43828 442/403 |
| 6,572,685 | B2 | 6/2003 | Dunshee | |
| 6,623,548 | B1 | 9/2003 | Gordon et al. | |
| 6,723,150 | B2 | 4/2004 | Parker | |
| 6,764,533 | B2 | 7/2004 | Lobiondo | |
| 6,805,732 | B1 * | 10/2004 | Billiotte | A61L 9/22 264/129 |
| 6,955,708 | B1 * | 10/2005 | Julos | F24F 8/194 422/186.04 |
| 6,984,259 | B2 | 1/2006 | Hurst | |
| 7,014,688 | B2 * | 3/2006 | Griffiths | B03C 3/14 55/DIG. 39 |
| 7,025,806 | B2 | 4/2006 | Coppom et al. | |
| 7,112,232 | B2 * | 9/2006 | Chang | F24F 13/28 55/467 |
| 7,112,238 | B2 | 9/2006 | Joannou | |
| 7,150,780 | B2 * | 12/2006 | Krichtafovitch | B03C 3/47 96/95 |
| 7,258,729 | B1 * | 8/2007 | Barsimanto | B03C 3/60 96/97 |
| 7,323,146 | B2 * | 1/2008 | Kim | B01D 46/10 422/186.06 |
| 7,364,607 | B2 | 4/2008 | Ueda et al. | |
| 7,367,997 | B1 | 5/2008 | Isogawa | |
| 7,445,654 | B2 | 11/2008 | Wong | |
| 7,452,410 | B2 | 11/2008 | Bergeron | |
| 7,455,706 | B2 | 11/2008 | Latham et al. | |
| 7,459,002 | B2 | 12/2008 | Kalous et al. | |
| 7,686,869 | B2 | 3/2010 | Wiser et al. | |
| 7,708,813 | B2 | 5/2010 | Wiser et al. | |
| 8,070,861 | B2 | 12/2011 | Wiser et al. | |
| 8,252,095 | B2 * | 8/2012 | Wiser | B03C 3/30 55/528 |
| 8,795,601 | B2 | 8/2014 | Wiser et al. | |
| 9,764,331 | B2 * | 9/2017 | Wiser | B03C 3/016 |
| 2002/0021194 | A1 | 2/2002 | Maehara et al. | |
| 2002/0170435 | A1 | 11/2002 | Joannou | |
| 2003/0000389 | A1 | 1/2003 | Schultheiss et al. | |
| 2004/0140194 | A1 * | 7/2004 | Taylor, Jr. | B01D 53/0446 422/186.04 |
| 2004/0144254 | A1 | 7/2004 | Wiser et al. | |
| 2004/0177759 | A1 | 9/2004 | Tsai et al. | |
| 2005/0045036 | A1 | 3/2005 | Vetter et al. | |
| 2005/0045037 | A1 | 3/2005 | Parisi et al. | |
| 2005/0108996 | A1 | 5/2005 | Latham et al. | |
| 2005/0150384 | A1 | 7/2005 | Krichtafovitch et al. | |
| 2005/0172812 | A1 | 8/2005 | Ueda et al. | |
| 2006/0042205 | A1 | 3/2006 | Kalous et al. | |
| 2006/0064953 | A1 | 3/2006 | Wong | |
| 2006/0137527 | A1 * | 6/2006 | Joannou | B03C 3/155 96/66 |
| 2006/0180023 | A1 | 8/2006 | Coppom et al. | |
| 2010/0326279 | A1 | 12/2010 | Wiser et al. | |

(56) References Cited

U.S. PATENT DOCUMENTS

| | | | |
|---|---|---|---|
| 2011/0002814 A1 | 1/2011 | Wiser | |
| 2014/0338536 A1 | 11/2014 | Wiser | |
| 2016/0144379 A1* | 5/2016 | Wiser | B03C 3/70 96/58 |

FOREIGN PATENT DOCUMENTS

| | | |
|---|---|---|
| DE | 3339828 | 5/1985 |
| EP | 229857 | 7/1987 |
| EP | 0585054 A | 3/1994 |
| FR | 2559684 | 8/1985 |
| GB | 2160447 | 12/1985 |
| GB | 2160447 B | 12/1985 |
| GB | 2329598 | 3/1999 |
| JP | 51027384 | 2/1976 |
| JP | 55024561 | 2/1980 |
| JP | 59228955 | 12/1984 |
| JP | 61008149 | 1/1986 |
| JP | 64056157 | 3/1989 |
| JP | 01307463 | 12/1989 |
| JP | 05093524 | 4/1993 |
| JP | 06007621 | 1/1994 |
| JP | 09010628 | 1/1997 |
| JP | 2001518378 A | 10/2001 |
| JP | 2003275526 | 9/2003 |
| JP | 3529122 B2 | 5/2004 |
| JP | 200505514 A | 3/2005 |
| JP | 2005055114 A | 3/2005 |
| JP | 05320926 | 11/2005 |
| KR | 19880000127 | 3/1988 |
| KR | 20020083565 | 11/2002 |
| KR | 20-0318828 Y1 | 7/2003 |
| KR | 20040034583 | 4/2004 |
| KR | 20040063390 | 7/2004 |
| RU | 2026751 | 1/1995 |
| SU | 2240856 | 12/1990 |
| WO | 0074818 | 12/2000 |
| WO | 0145851 | 6/2001 |
| WO | 2004028698 | 4/2004 |
| WO | 2004073823 A2 | 9/2004 |

OTHER PUBLICATIONS

Final Office Office Action issued in U.S. Appl. No. 15/708,201, mailed Jul. 1, 2020, 9 pages.
Non Final Office Action issued in U.S. Appl. No. 15/708,201, mailed Nov. 19, 2019, 11 pages.
Notice of Allowance issued in U.S. Appl. No. 14/451,531, mailed May 19, 2017, 9 Pages.
Non Final Office Action issued in U.S. Appl. No. 14/451,531, mailed Jun. 2, 2016, 9 Pages.
Notice of Allowance issued in U.S. Appl. No. 13/584,320, mailed May 28, 2014, 5 Pages.
Notice of Allowance issued in U.S. Appl. No. 13/584,320, mailed Apr. 8, 2014, 8 Pages.
Requirement for Restriction/Election issued in U.S. Appl. No. 13/584,320, mailed Dec. 4, 2013, 7 Pages.
Notice of Allowance issued in U.S. Appl. No. 12/732,626, mailed May 2, 2012, 5 Pages.
Non Final Office Action issued in U.S. Appl. No. 12/732,626, mailed Jun. 30, 2011, 8 Pages.
Requirement for Restriction/Election issued in U.S. Appl. No. 12/732,626, mailed Dec. 3, 2010, 7 Pages.
Decision to Grant a Patent Translation issued in Korean Patent Application No. 10-219-7001397, May 25, 2021, 1 page.

* cited by examiner

FILTER MEDIA FOR ACTIVE FIELD POLARIZED MEDIA AIR CLEANER

FIELD OF THE INVENTION

The present invention relates generally to air cleaning systems and is particularly directed to filter media for air cleaners of the type that use an electrostatic field to polarize a media and to polarize particles to increase the particle collection efficiency on the media.

BACKGROUND OF THE INVENTION

The principal of electrostatic attraction has been used for many years to enhance the removal of contaminants from air streams. There are three primary categories of air electrostatic cleaners: electrostatic precipitators, passive electrostatic filters and active field polarized media air cleaners, which are sometimes known under different terms.

Electrostatic precipitators charge particles and then capture them on oppositely charged and/or grounded collection plates.

A passive electrostatic filter (also know as an electret) employs a media (or combination of different media) that through some combination of treatment and/or inherent properties has an electrostatic charge. Particles entering the filter media that have an electrostatic charge are attracted to the charged media filter materials that have the opposite electrostatic charge.

An active field polarized media air cleaner uses an electrostatic field created by a voltage differential between two electrodes. A dielectric filter media is placed in the electrostatic field between the two electrodes. The electrostatic field polarizes both the media fibers and the particles that enter, thereby increasing the efficiency of the media and the air cleaner. A dielectric material is an electrical insulator or a substance that is highly resistant to electric current that can also store electrical energy. A dielectric material tends to concentrate an applied electric field within itself and is thus an efficient supporter of electrostatic fields.

A further electrostatic air filter design is disclosed in Canadian Patent No. 1,272,453, in which a disposable rectangular cartridge is connected to a high voltage power supply. The cartridge consists of a conductive inner center screen, which is sandwiched between two layers of a dielectric fibrous material (either plastic or glass). The two dielectric layers are, in turn, further sandwiched between two outer screens of conductive material. The conductive inner center screen is raised to a high voltage, thereby creating an electrostatic field between the inner center screen and the two conductive outer screens that are kept at an opposite or ground potential. The high voltage electrostatic field polarizes the fibers of the two dielectric layers.

The air cleaners may be installed in a variety of configurations and situations, both as part of a heating ventilating and air conditioning (HVAC) system and in standalone air moving/cleaning systems. In smaller HVAC systems (e.g. residential and light commercial), the air cleaner panels are often installed in a flat configuration (perpendicular to the airflow) or in angled filter tracks. In larger systems, banks of air filters are typically arranged in a V-bank configuration where multiple separate filters are positioned to form a Z-fold filter perpendicular to the axis of airflow.

SUMMARY OF THE INVENTION

The invention is embodied in several individual improvements to filter media for active field polarized media air cleaners and combinations thereof. The individual features of the present invention are as follows:

1. In particular, the filter media of the present invention includes two layers of fibrous dielectric material (such as polyester) with a higher resistance air permeable material (such as a fiberglass screen) sandwiched between the lower resistance dielectric (polyester) layers.

2. In another embodiment of the present invention, the filter media includes a layer of fibrous dielectric material forming a mixed fiber layer having fibers from different ends of the triboelectric series of materials (triboelectric scale) for use in an active field polarized media air cleaner.

3. In yet another embodiment of the present invention, the filter media includes a layer of relatively higher density dielectric material (such as fibrous polyester), followed by a layer of relatively lower density material (such as less dense fibrous polyester).

DETAIL DESCRIPTION

Figure 1:
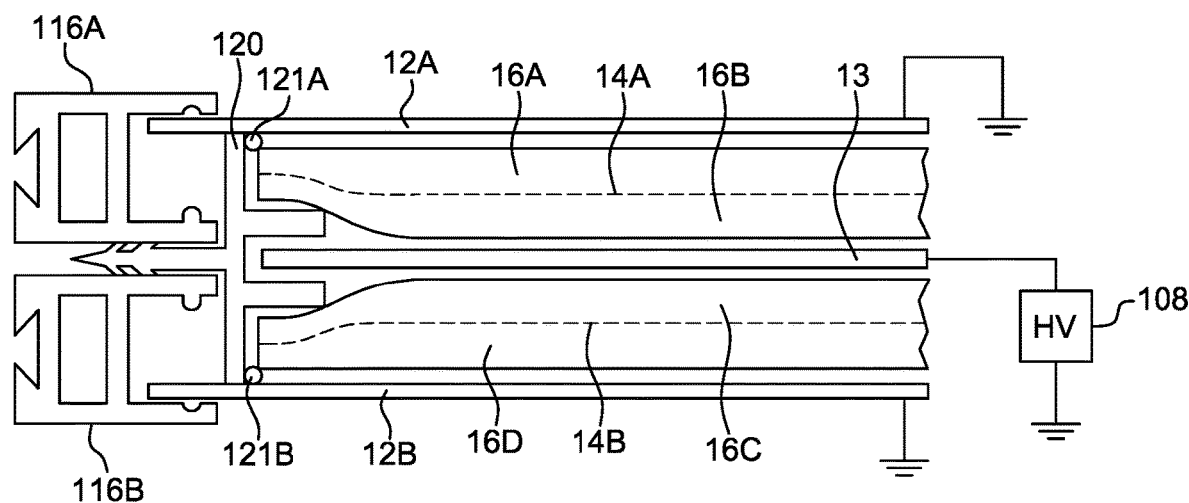
FIG. 1 is a cross-sectional diagram of filter media incorporating a higher resistance air permeable screen between fibrous pads of dielectric material having a relatively lower resistance in accordance with the present invention.

An embodiment of an active field polarized media air cleaner in accordance with the present invention is shown in FIG. 1. In FIG. 1 (as in FIGS. 2-7) airflow through the filter is downward from the top of the diagram to the bottom of the diagram. The filter consists of a frame that holds the filter media.

In one embodiment of the invention, the filter media itself consists of a dielectric media support frame 120, a first pad of fibrous dielectric material 16A, fiberglass mesh screen 14A, a second pad of fibrous dielectric material 16B, a center screen 13, a third pad of fibrous dielectric material 16C, another fiberglass mesh screen 14B and a fourth pad of dielectric filter material 16D. The filter frame that holds the filter media consists of a first conductive holding frame 116A with a first conductive outer screen 12A, and a second conductive holding frame 116B with a second conductive outer screen 12B. While for the sake of clarity, the same basic configuration using the media frame 120 and holding frames 116A,B, are used for drawings, these are but one possible embodiment. The essential elements of the current invention are the various configurations of media between two electrodes in a polarized media air cleaner. While there are certain advantages to the specific embodiments disclosed in the illustrations, the center screen need not go all the way to the edge, nor have a frame around-it and the media layers.

The first pad of dielectric filter material 16A is attached to the dielectric media support frame 120 and/or the center electrode 13 by a suitable means such as adhesive material 121A or ultrasonic welding. The fourth pad of dielectric filter material 16D is attached to the dielectric media support frame 120 by a suitable means, such as adhesive material 121B or ultrasonic welding. In embodiments with no media support frame, the various layers of media 16A-D and 14A and B and center screen 13 would be typically be attached together by a suitable means such as adhesives, ultrasonic welding, sewing or clamping. The first conductive outer screen 12A is held in place by a first conductive holding frame 116A. The second conductive outer screen 1213 is held in place by a second conductive holding frame 116B.

In operation, one terminal of a high voltage power supply 108 is connected to center screen 13. The other terminal of the high-voltage power supply 108 is coupled to the first conductive outer screen 12A and the second conductive outer screen 12B, which is held typically at ground potential.

Particles in the incoming air passing through dielectric filter material 16A, 16B, 16C and 16D of the active field polarized media air cleaner of FIG. 1 are polarized by the electric field therein and collected on the first and second pads of dielectric filter material 16A, 16B, 16C and 16D.

Filter media of the present invention include two layers of fibrous dielectric material with a higher resistance air permeable material sandwiched between the lower resistance dielectric layers. While other material combinations are possible, specifically, in FIG. 1 a fiberglass screen 14A is sandwiched between polyester layer 16A and polyester layer 16B, which is disposed above the center screen 13. Similarly, below the center screen 13 is a fiberglass screen 14B sandwiched between polyester layer 16C and polyester layer 16D.

It has been found that this disposition of materials allows for a higher and more stable voltage differential between the electrodes. This increases particle removal efficiencies as higher voltage means higher field strength and therefore higher efficiencies. Specifically, it has been found the above disposition of materials allows for up to a 25% higher voltage without arcing and spraying between electrodes.

Filter media of the present invention include a mixed fiber layer in an active field polarized media air cleaner, said mixed fiber layer having fibers from different parts of the triboelectric series of materials. Most materials will generate and store some static electricity. The capacity of the material to generate and store an electric charge defines where it belongs on the triboelectric scale.

Triboelectric Series of Materials Causing Static Electricity

Some materials create more static electricity than others. Since static electricity is the collection of electrically charged particles on the surface of a material, various materials have a tendency of either giving up electrons and becoming positive (+) in charge, or attracting electrons and becoming negative (-) in charge. The triboelectric series is a list of materials, showing which have a greater tendency to become positive (+) and which have a greater tendency to become negative (-). The list is used to determine which combinations of materials create the most static electricity.

For illustration purposes, some common materials are listed below according how well they create static electricity when rubbed with another material, as well as what charge the material will possess. The list is not an exhaustive list and every material fits somewhere is the positive or negative triboelectric scale.

Materials that Become Positive in Charge

The following materials will tend to give up electrons when brought in contact with other materials. They are listed from those with the greatest tendency to give electrons to those that barely give up electrons.

|  | Comments |
| --- | --- |
| Dry human skin | Greatest tendency to giving up electrons and becoming highly positive (+) in charge |
| Leather | |
| Rabbit fur | Fur is often used to create static electricity |
| Glass | The glass on your TV screen gets charged and collects dust |
| Nylon | |
| Wool | |
| Lead | A surprise that lead would collect as much static electricity as cat fur |
| Cat fur | |
| Silk | |
| Aluminum | Gives up some electrons |
| Paper | |

Materials that are Neutral

There are very few materials that do not tend to readily attract or give up electrons when brought in contact or rubbed with other materials.

|  | Comments |
| --- | --- |
| Cotton | Best for non-static clothes |
| Steel | Not useful for static electricity |

Materials that Become Negative in Charge

The following materials will tend to attract electrons when brought in contact with other materials. They are listed from those with the least tendency to attract electrons to those that readily attract electrons.

|  | Comments |
| --- | --- |
| Wood | Attracts some electrons, but is almost neutral |
| Amber | |
| Hard rubber | Some combs are made of hard rubber |
| Nickel, Copper | Copper brushes used in Wimshurst electrostatic generator |
| Brass, Silver | |
| Gold, Platinum | It is surprising that these metals attract electrons almost as much as polyester |
| Polyester | Clothes have static cling |
| Styrene (Styrofoam) | Packing material seems to stick to everything |
| Saran Wrap | You can se how Saran Wrap will stick to things |
| Polyurethane | |
| Polyethylene (like Scotch Tape) | Pull Scotch Tape off surface and it will become charged |
| Polypropylene | |
| Vinyl (PVC) | Many electrons will collect on PVC surface |
| Silicon | |

-continued

| | Comments |
|---|---|
| Teflon | Greatest tendency of gathering electrons on its surface and becoming highly negative (−) in charge |

The best combinations of materials to create static electricity would be one from the positive charge list and one from the negative charge list. However, a moderate amount of static electricity can be created from two materials on the positive charge list or two materials on the negative charge list. For example, when two materials that tend to give up electrons are rubbed together, the one with the greatest tendency will moderately become positive (+) in charge. Likewise, when two materials that tend to attract electrons are rubbed together, the one with the greatest tendency will moderately become negative (−) in charge.

Figure 2:
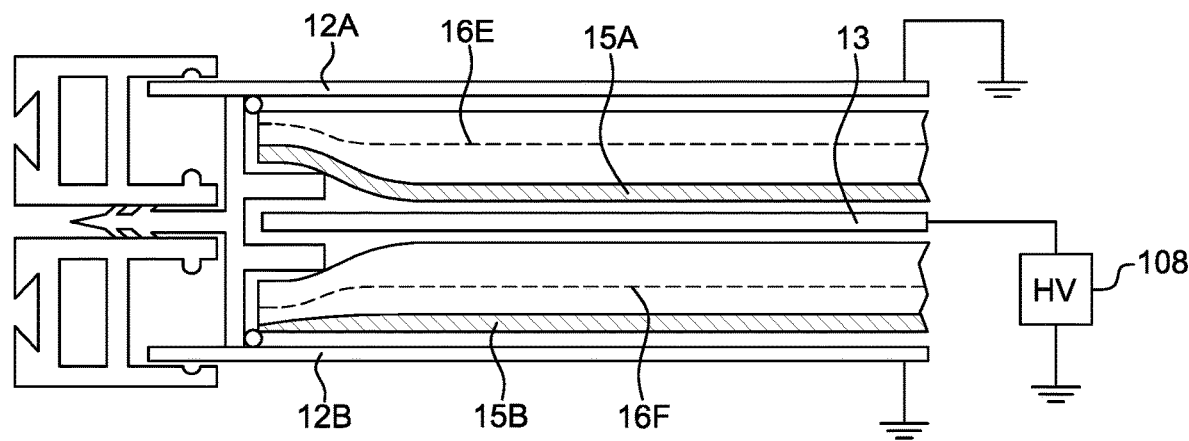
FIG. 2 is a cross-sectional diagram of filter media incorporating a fibrous pad of dielectric material and a mixed fiber layer having fibers from different ends of the triboelectric scale in accordance with the present invention.

A filter media of the present invention for use in an active field polarized media air cleaner using a mix of fibers from different parts and/or preferably different sides of the triboelectric scale is shown in FIG. 2. Specifically, filter layer 15A contains a mix of fibers from different sides of the triboelectric scale (mixed triboelectric filter layer). The different fibers of filter layer 15A may be interwoven and mixed together throughout filter layer 15A, or in the alternative, the different fibers of filter layer 15A may be first and second separate sheets of filter material placed in contact with each other. That is, a first sheet of filter material is made of fibers from one side of the triboelectric scale and a second sheet of filter material is made of fibers from the other side of the triboelectric scale. The first and second sheets of filter material are placed in contact with each other to form the mixed triboelectric filter layer' 15A.

Mixed triboelectric filter layer 15B is similar to mixed triboelectric filter layer 15A. The important feature of mixing together (by interweaving or bringing into contact) fibers from different sides of the triboelectric scale is that the mixture of such fibers produces sits of relative positive and negative charge on the fibers within such mixed triboelectric fiber layers 15A, 15B. Such integrated materials are available and are available from, among others, Alhstrom Air Media who's HP series of material is a mix of modacrylic and polypropylene and Hollingsworth and Vose who's Technostat materials are a mix of acrylic and polypropylene.

It is well known in the manufacture and design of passive electrostatic filters that the proper mix of materials from different sides of the triboelectric scale will boost the efficiency of the media beyond what would be anticipated solely from the density of the media, i.e. from the passive mechanisms of the media. Other types of passive electrostatic filters have charges imposed on the media by a variety of techniques. One issue with passive electrostatic filters is that the initial efficiencies due to electrostatic attraction actually decline as the fibers become covered with contaminants and/or gradually discharge due to a variety of factors (humidity, chemicals, and temperature).

While putting many filter medias in an electrostatic field can increase their efficiency, this is not universally the case. In fact, many passive electrostatic media show no improvement or actually perform worse. However, it has been found that putting triboelectric type electret media in a polarizing field does improve its effectiveness and eliminate the efficiency dip that is seen. The triboelectric layer tends to be relatively thin, it may therefore be used in one or more layers, together or separate, at various positions within the air cleaner media, i.e. with other media materials positioned on either or both sides of it.

In another embodiment of the present invention, above the mixed triboelectric filter layer 15A is a relatively sparse fibrous layer 16E. The filter media structure above the center screen 13 is repeated below the center screen 13, namely a second relatively sparse fibrous layer 16F above a second mixed triboelectric filter layer 15B. The relatively sparse layers could be a variety of materials or different materials from each other.

Figure 3:
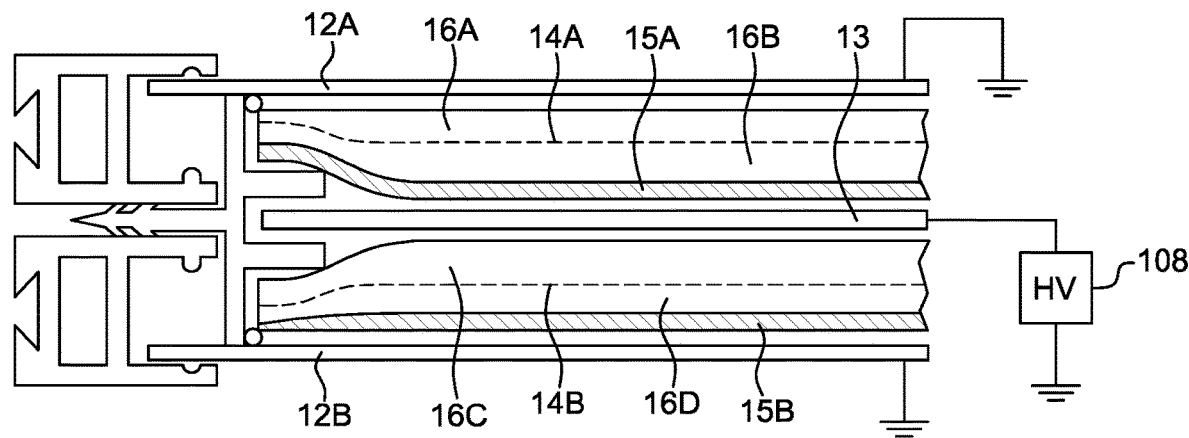
FIG. 3 is a cross-sectional diagram of filter media incorporating features from FIGS. 1 and 2 in accordance with the present invention.

A filter media of the present invention for use in an active field polarized media air cleaner which combines both a fiberglass center screen 14A, 14B and a mix of fibers from different sides of the triboelectric scale is shown in FIG. 3. The filter media in FIG. 3 is a combination of the filter media shown in FIGS. 1 and 2.

This combination combines the benefits of each embodiment, allowing for the for maximum system efficiency.

Figure 4:
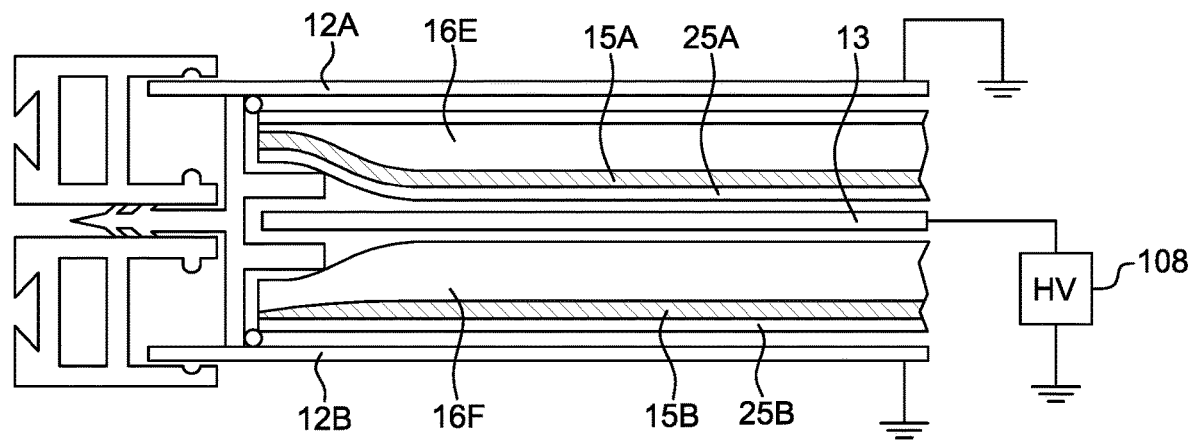
FIG. 4 is a cross-sectional diagram of filter media incorporating a layer of higher density dielectric material followed by a lower density dielectric material in accordance with the present invention.

A filter media incorporating a layer of higher density dielectric material followed by layer of low density dielectric material is shown in FIG. 4. The filter media shown in FIG. 4 is similar to that shown in FIG. 2. However in FIG. 4, an additional filter layer 25A of relatively lower density material is disposed after filter layer 16E, which is of relatively higher density material.

Figure 5:
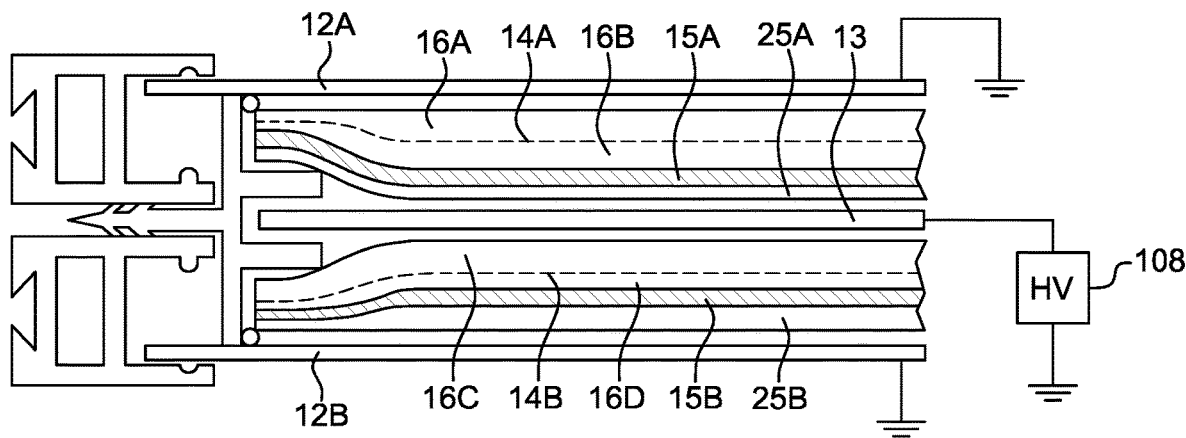
FIG. 5 is a cross-sectional diagram of filter media incorporating features from FIGS. 1 through 4 in accordance with the present invention.

Another filter media incorporating a layer of lower density dielectric material following a layer of higher density dielectric material is shown in FIG. 5. The filter media shown in FIG. 5 is similar to that shown in FIG. 3. However, in FIG. 5 an additional filter layer 25A of relatively less dense material is positioned after filter layer 16B. Additionally, in FIG. 5 a second triboelectric filter layer 25B of relatively less dense material is placed after filter layer 16D at the end of the airflow through the active field polarized media air cleaner.

The benefit of these embodiments is a reduction in resistance to airflow. The densest layer of media will have the highest resistance to airflow. If the densest layer is against one of the electrodes, its area will be effectively reduced by that of the electrode. This would increase the air velocity through the remaining area and increase the resistance to airflow. By putting a less dense layer between the electrode and the densest layer, it increases the air speed through the less dense material instead of the denser material thereby reducing resistance to airflow significantly.

Figure 6:
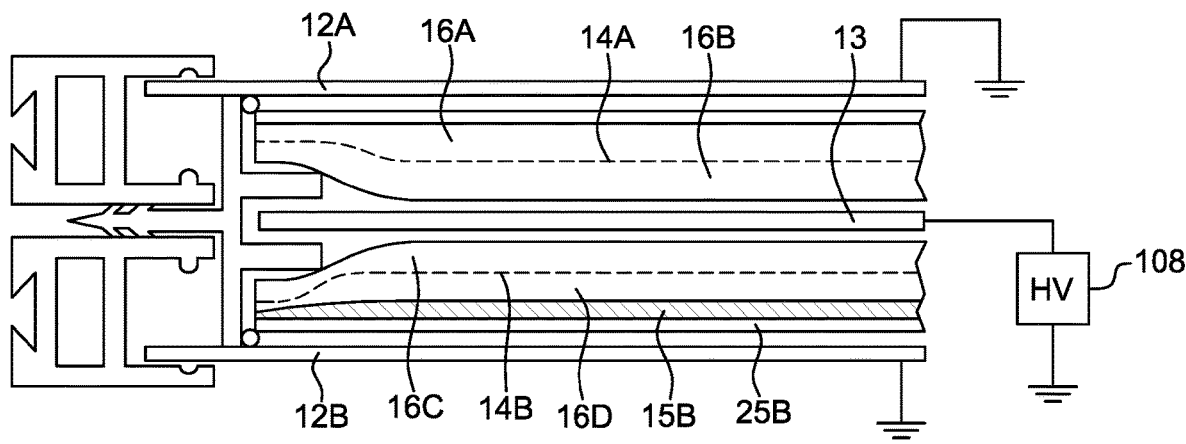
FIG. 6 is a cross-sectional diagram of filter media incorporating features from FIGS. 1 and 5 in accordance with the present invention.

In FIG. 6, the portion of the filter media above the center screen 13 is the same as that shown in FIG. 1; the portion of the filter media below the center screen 13 is the same as that shown in FIG. 5.

This embodiment provides superior loading characteristics. By capturing the larger particles or particles of lower density and/or lower momentum, on the less dense upstream layers, the more dense layers do not become clogged and are able to collect primarily the smaller (i.e., higher density and/or higher momentum) particles and therefore have a longer service life. The media thus allows a homogenous distribution of particulate through the volume of the media.

Figure 7:
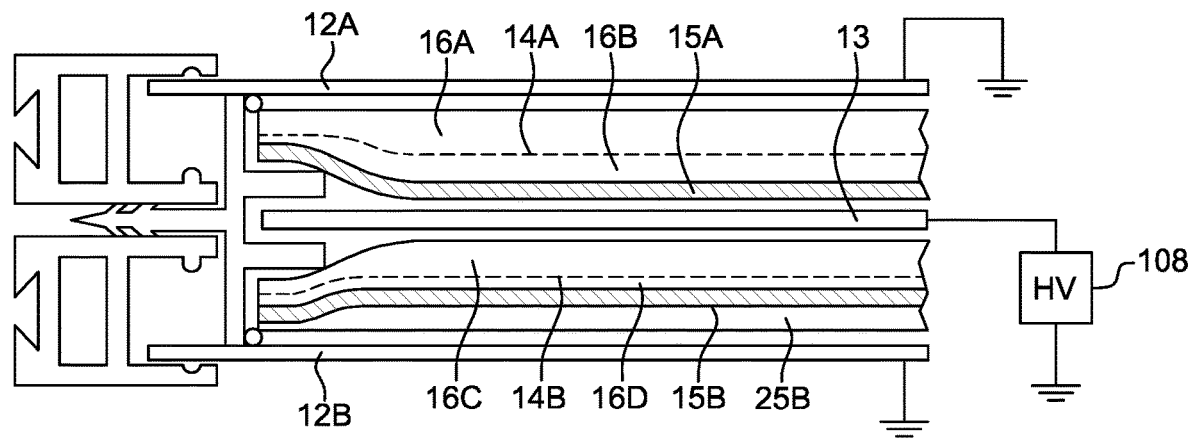
FIG. 7 is a cross-sectional diagram of a filter media incorporating features from FIGS. 3 and 6 in accordance with the present invention.

In FIG. 7, the portion of the filter media above the center screen 13 is the same as that shown in FIG. 3; the portion of the filter media below the center screen 13 is the same as that shown in FIG. 5 or 6.

Figure 8:
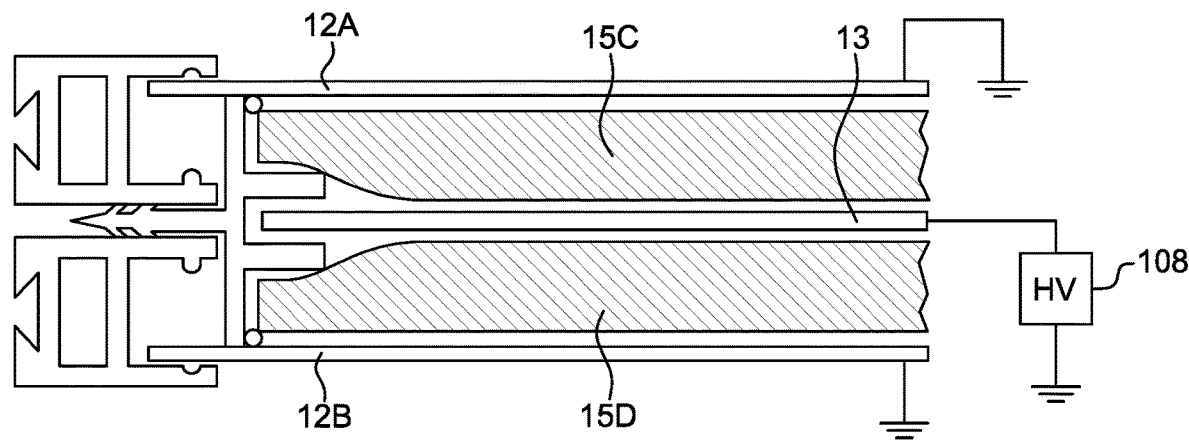
FIG. 8 is a cross-sectional diagram of filter media incorporating a mixed fiber layer having fibers from different ends of the triboelectric scale in accordance with the present invention.
Figure 9:
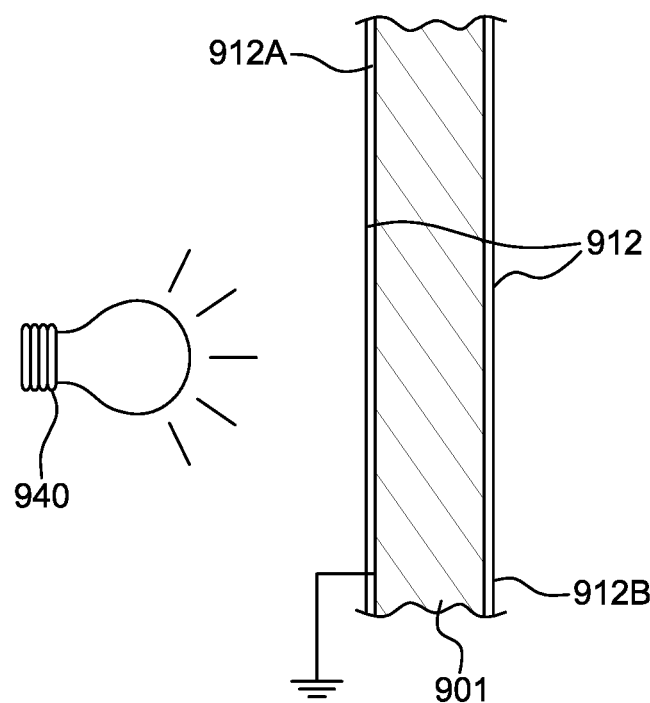
FIG. 9 shows a photocatalytic device embodiment.
Figure 10:
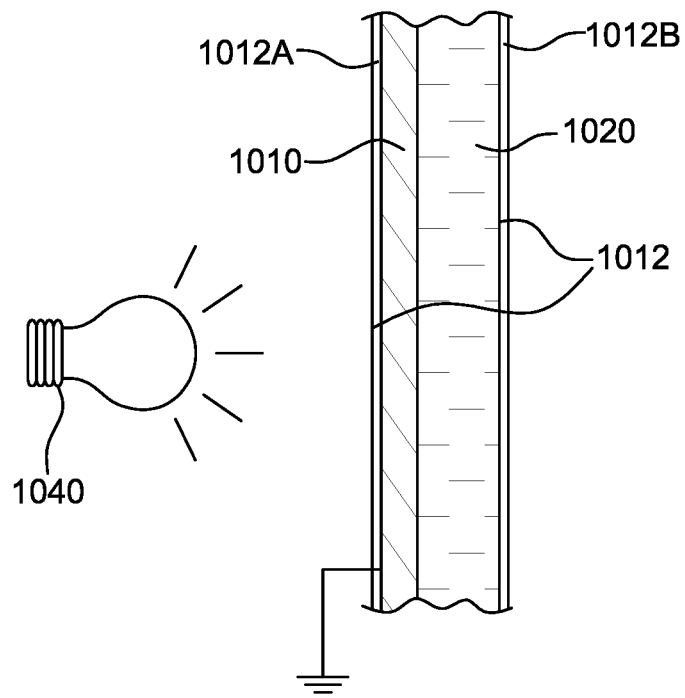
FIG. 10, shows an alternative photocatalytic device embodiment.

In FIG. 8, the filter media 15C, 15D above the center screen 13 is a mixed fiber layer having fibers from different ends of the triboelectric scale in accordance with the present invention.

In a further embodiment of the invention, one of the outer most layers of media could be treated with a photocatalytic material. The air cleaner could then be coupled with a UV light for the breakdown of gas phase contaminants. Hydroxyls produced in this embodiment could inactivate biologicals and breakdown gas phase contaminants. In such an embodiment, under the influence of UV light, the media creates hydroxyl radicals and super-oxide ions to react with the captured and airborne bioaerosols and gas phase contaminants. The photocatalytic layer could be the furthest downstream layer. This would keep it substantially free of particle contamination.

In a further embodiment of the invention, the external screen/electrode of the filter frame is treated with the photo catalyst.

In a further embodiment of the invention the center screen would have odor absorbing properties, such as a carbon impregnated foam or mesh.

The downstream layer of lower density material could be treated with a catalyst for breaking down VOC's, other reactive gas phase contaminants and/or Ozone and/or biological contaminants.

At least one of the external screens and/or a layer of media can be treated with a photocatalyst that tends to destroy gaseous impurities such as VOC's and biological contaminants in the presence of light, typically UV light. The latter configuration could be coupled with one or more UV sources in close proximity to thereby bring about the photocatalytic effect. The resulting integration of components would significantly reduce the cost of applying photocatalysis to the air stream. The catalyst may be applied to either the upstream or the downstream screen. The system may include central UV lights to shine on treated screens both upstream and downstream of the treated screens. In the case of applying the photocatalyst to a layer of media, the preferred embodiment would be to have it be the most downstream layer, as this layer would be less likely to be fouled by contaminants.

FIG. 9 shows a photocatalytic device embodiment. Photocatalytic Oxidation (PCO) has been used to purify various liquid and gas streams but in PCO, there is sometimes an issues where the catalyst may not adhere to the substrate onto which it has been applied and PCO process efficiency. Titanium dioxide may be used as the photocatalyst that coats the filter or electrodes so that PCO may be used to purify the stream.

As shown in FIG. 9. placing the substrate within an electrostatic field results in both better adherence of the catalyst to the substrate 901 and a quicker reaction time. For example, as shown in FIG. 9, if the catalyst is applied to a non-woven fiberglass material 901 and that material is placed between two electrodes 912A, 912B with a voltage differential of 5-15 kv dc and spaced approximately 0.5" s apart, under a UV light source 940, the catalyst is held onto the fiberglass material 901 by the resultant polarizing field and shed less readily. Further, the energy of the field itself speeds the breakdown of volatile compounds in the airstream.

In preliminary testing, TVOC levels were brought down almost twice as quickly with the same catalyst when it was placed in an electrostatic field. The experiment was as follows: A u-shaped duct with fan were configured to draw and return air from and to an approximately 1,000 cubic foot room. Tolulene was poured on a cloth and the cloth left in the space for several minutes. An Aircuity Optima unit was used to measure TVOC levels in the room. A V-bank air cleaner was placed in the duct with a 254 urn UVC lamp upstream. A circulating fan was set to 1,000 cfm. The air cleaner frames could hold a media and were able to create and electrostatic field inside the media. After 25 minutes, with no filter, TVOC levels dropped 6%. With UV lamp on and a catalyst coated media with no electrostatic field, there was a 12% drop. With the same arrangement and the electrostatic field energized, there was a 24% drop.

Such a device could be applied to a variety of HVAC and air moving systems for purification of the airstream. The catalyst could also be applied to a woven material and could be a variety of materials other than glass. The catalyst coated material could be sprayed or dipped in the catalyst.

In another embodiment shown in FIG. 10, the catalyst coated material 1012 could be one layer of a multiple layer filter media containing both the coated material 1012 and a non-coated layer 1020 between electrodes 1012A, 1012B in the presence of a UV light source 1040*s*.

The electrodes could be made from a variety of conductive materials and may be electrically uniform and include evenly spaced grids on either side of the coated media material. Further they may be as open as possible to allow the maximum light penetration into the coated material. The electrodes themselves could be coated with the catalyst as well.

In all cases, the device may be put in close proximity to a UV light source(s) to supply primary energy for the catalytic reaction. Hydroxyls produced in this scenario could inactivate biologicals and breakdown gas phase contaminants. In such an embodiment, under the influence of UV light, the media creates hydroxyl radicals and super-oxide ions to react with the captured and airborne bioaerosols and gas phase contaminants.

While the inventions described above have made reference to various embodiments, modifications can be made to the structure and elements of the invention without departing from the spirit and scope of the invention as a whole. In particular, various layers or elements could be combined or repeated to achieve various effects. For example, while one figure shows the basic concept of the air cleaner, another figure shows the configuration of one type of assembled system. While for the sake of clarity, the various elements have been shown as separate layers, two or more of the "layers" may be combined into a single layer or material.

The invention(s) disclosed above could be used in variety of ways, including, but not limited to, use in HVAC systems, self-contained filter/fan units, and industrial air cleaning systems, and dust collectors. While the above embodiments primarily describe flat filter configurations, the inventions could be adapted to other configurations as well, including but not limited to V-bank groupings of multiple flat panels, interconnected groupings of panel and V-Bank units and cylindrical filters for dust collection systems.

What is claimed is:

1. An active field polarized media air cleaner comprising:

a first conductive outer screen;

a second conductive screen substantially parallel to the first conductive outer screen;

a pad of material, the pad of material being disposed between the first conductive outer screen and the second conductive screen, wherein the pad of material and the first conductive outer screen and the second conductive screen are adjacent to one another, wherein the pad of material comprises multiple layers and at least one of the multiple layers is a different material from another of the multiple layers, wherein the different materials include materials combinations that create static electricity therebetween; and a high-voltage power supply having first and second terminals, the first terminal of said high voltage power supply being connected to the second conductive screen, the second terminal of the high-voltage power supply being coupled to the first conductive outer screen.

2. The active field polarized media air cleaner of claim 1, wherein the pad of material comprises fibrous polyester.

3. The active field polarized media air cleaner of claim 1, wherein the pad of material fiberglass.

4. The active field polarized media air cleaner of claim 1, wherein the pad of material a non-woven material.

5. The active field polarized media air cleaner of claim 1, wherein the pad of material is subject to UV light.

6. The active field polarized media air cleaner of claim 1, wherein at least one of the layers is treated by a photocatalyst.

7. The active field polarized media air cleaner of claim 1, wherein the first conductive outer screen, second conductive screen, and pad of material are all contained within a single filter frame.

8. The active field polarized media air cleaner of claim 7, wherein the high-voltage power supply is located separate from, but connected to, the first conductive outer screen and the second conductive screen.

9. An active field polarized media comprising:
a first conductive outer screen;
a second conductive screen;
a pad of material, the pad of material being disposed between the first conductive outer screen and the second conductive screen, wherein the pad of material comprises multiple layers and at least one of the multiple layers is a different material from another of the multiple layers, wherein the different materials include materials combinations that create static electricity therebetween;
wherein the pad of material and the conductive outer screen and the second conductive screen are contained within a filter frame; and
a high-voltage power supply having first and second terminals, the first terminal of said high voltage power supply being connected to the second conductive screen the said second terminal of the high-voltage power supply being coupled to the first conductive outer screen.

10. The active field polarized media of claim 9, wherein the pad of material comprises fibrous polyester.

11. The active field polarized media of claim 9, wherein the pad of material comprises fiberglass.

12. The active field polarized media of claim 9, wherein the pad of material comprises a non-woven material.

13. The active field polarized media of claim 9, wherein the pad of material comprises subject to UV light.

14. The active field polarized media of claim 9, wherein at least one of the layers is treated by a photocatalyst.

* * * * *